United States Patent
Näslund

(10) Patent No.: US 8,406,854 B2
(45) Date of Patent: Mar. 26, 2013

(54) MARKER FOR POSITIONING IN BODY TISSUE

(76) Inventor: Ingemar Näslund, Huddinge (SE)

( * ) Notice: Subject to any disclaimer, the term of this patent is extended or adjusted under 35 U.S.C. 154(b) by 1258 days.

(21) Appl. No.: 11/571,705

(22) PCT Filed: Jul. 5, 2005

(86) PCT No.: PCT/SE2005/001111
§ 371 (c)(1),
(2), (4) Date: Nov. 13, 2007

(87) PCT Pub. No.: WO2006/004542
PCT Pub. Date: Jan. 12, 2006

(65) Prior Publication Data
US 2008/0058769 A1    Mar. 6, 2008

(30) Foreign Application Priority Data

Jul. 5, 2004 (SE) .......... 0401738
Sep. 14, 2004 (SE) .......... 0402188

(51) Int. Cl.
*A61B 5/05* (2006.01)

(52) U.S. Cl. ........ 600/426; 600/407; 600/424; 600/425; 600/436

(58) Field of Classification Search .......... 128/657, 128/772, 899; 604/95.03–95.04, 170.01–170.03; 600/424, 431, 436
See application file for complete search history.

(56) References Cited

U.S. PATENT DOCUMENTS

| | | | |
|---|---|---|---|
| 5,221,269 A | 6/1993 | Miller et al. | |
| 5,507,729 A * | 4/1996 | Lindenberg et al. | 604/170.01 |
| 6,056,700 A | 5/2000 | Burney et al. | |
| 7,125,420 B2 | 10/2006 | Rourke et al. | |
| 7,197,363 B2 | 3/2007 | Prakash et al. | |
| 2002/0059938 A1 | 5/2002 | Fogarty et al. | |
| 2003/0195433 A1 | 10/2003 | Turovskiy et al. | |

FOREIGN PATENT DOCUMENTS

| | | |
|---|---|---|
| EP | 0 393 972 | 10/1990 |
| EP | 0 395 997 | 11/1990 |
| JP | 61-67710 | 5/1986 |
| JP | 2-302253 | 12/1990 |
| JP | 05-038342 | 2/1993 |
| JP | 2003-290234 | 10/2003 |

(Continued)

OTHER PUBLICATIONS

Japanese Patent Office, English Translation of Japanese Office Action for JP Patent Application No. 519173/2007. Issued Aug. 16, 2010.

(Continued)

*Primary Examiner* — Tse Chen
*Assistant Examiner* — Mark Remaly
(74) *Attorney, Agent, or Firm* — Stites & Harbison PLLC; Douglas E. Jackson

(57) ABSTRACT

The present invention relates to a marker to be used inside human or animal body, comprising an elongated wire of a radiation retarding and/or radioactive material, wherein the wire is arranged with at least one bending means, capable of bending the wire upon insertion in human tissue. The invention also relates to a penetration needle to be used with the marker as well as a tool for facilitating the insertion and creation of the marker according to the invention.

8 Claims, 4 Drawing Sheets

FOREIGN PATENT DOCUMENTS

| WO | WO 98/01068 | 1/1998 |
|---|---|---|
| WO | WO-00/24320 | 5/2000 |
| WO | WO 01/28434 | 4/2001 |
| WO | WO 03-088806 | 10/2003 |

OTHER PUBLICATIONS

European Patent Office, Supplementary European Search Report for EP Application No. EP 05 75 7133, Nov. 30, 2010.

Japanese Patent Office, English Translation of Office Action issued in Japanese Patent Application No. 519173/2007, Jan. 18, 2011.

Official Action (Questioning) for Japanese Application No. 2007-519173, Appeal No. 2012-011489, Jul. 31, 2012, Japanese Patent Office.

* cited by examiner

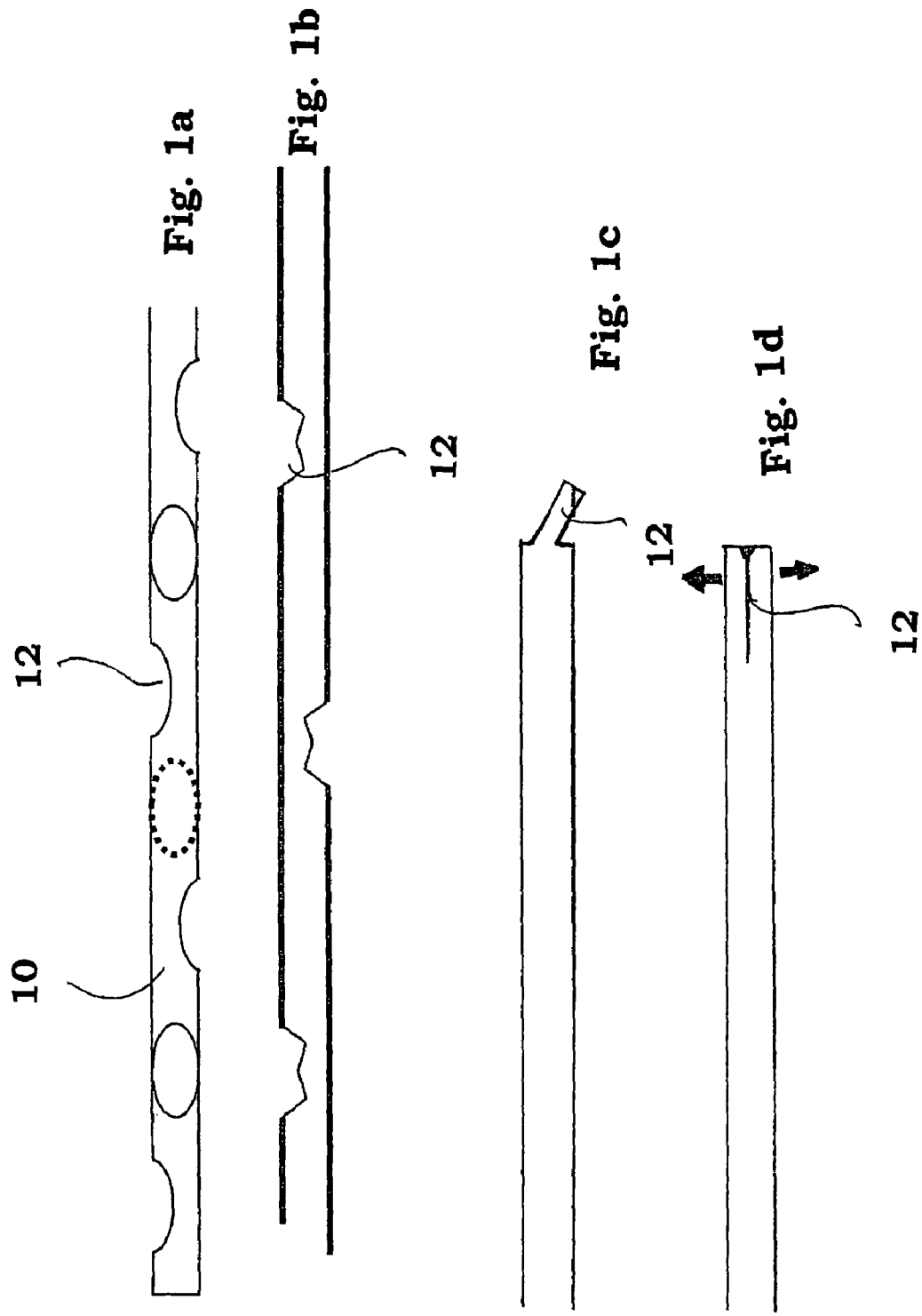

MARKER FOR POSITIONING IN BODY TISSUE

TECHNICAL AREA

The present invention relates to a fiducial marker to be used in human or animal tissue, in particular for marking the location of a tumour.

BACKGROUND OF THE INVENTION

Markers are used today for visualizing where a tumour is or has been located with for example x-ray. The marker is placed in a needle that is sterilized. The tip of the needle is advanced into the tumour and the marker is pushed out of the needle with a mandrin, i.e. a wire movable inside a cannula or pipe.

In connection with surgery, a so called clip may be attached to the tissue where the tumour has been. The markers may be left in the body and are often of some sort of inert material with high density in order to facilitate the imaging with the help of x-ray.

In connection with radio-therapy, the patient is often positioned with the aid of markers on the skin. This leads to great uncertainty regarding positioning due to movement of the skin in relation to inner organs. By producing x-ray images the skeleton may give guidance regarding the position of the therapy ray. Inner organs move also in relation to the skeleton and skeleton x-ray does not always give the correct guidance regarding the position of the tumour at the actual time when the x-ray image is taken. Soft tissue is not recorded with conventional x-ray. This may be done with the aid of computer tomography.

Ideally it is desirable to be able to position the tumour securely in relation to the interception point of the central beam from different directions of radiation, the point which is called the iso-centre. If this can be done, large safety margins do not have to be added, which margins may amount to several centimeters. The volumes of the margins often become large in relation to the volume of the tumour, a volume of normal tissue that should no be radiated. Markers on the skin may be relatively accurate in 75 percent of the radiation cases while precision radiation requires refined methods. Several methods are on the process, for example breath gating, which means that the location of the tumour is estimated during different breathing phases. This is an indirect method that is time consuming and ineffective regarding resources and precision. There are equipment today that enables computer tomography on the radiation treatment table for locating the tumour at each treatment occurrence. This is also partly time consuming and requires the presence of a physician. The only direct method for positioning of tumours with precision, that also is cost-effective, is markers.

Markers in the tumour or in its vicinity is a valuable aid for positioning. The drawback is that it requires a certain mass in order to retard high energy x-ray beams for sufficient contrast on films or portal images, which leads to that the marker has to be relatively large. It requires a relatively thick needle that cannot be entered easily in any part of the body. A usual dimension of a gold marker is 1.0×3.0 mm. Such large needles for positioning markers can not penetrate all parts of the human body without the risk of internal bleeding, infection and the need for anaesthesia.

Markers are however relatively new in use. The therapy beam with energies of 4-50 MV (megavolt) provides a weak contrast of skeleton parts, providing difficulties in evaluating skeleton and markers during treatment. Several of the manufacturers of accelerators used during treatment have developed conventional x-ray add-ons on the accelerators. With this technology new possibilities and a new market are created for x-ray dense markers. High density retards x-ray radiation very well. A marker of silver has enough density for kilovolt x-ray, providing a good contrast but 24 carat gold is soft and is very suitable in this aspect. If one wants a visible marker with a therapy beam of several megavolt, then it is the mass that is important and not the density itself. In this aspect gold is more suitable than silver.

BRIEF DESCRIPTION OF THE INVENTION

The aim of the present invention is to provide a marker for use in x-ray therapy that provides good precision, is easy to arrange inside the body with reduced inconvenience for the patient and is securely attached to the tissue.

According to a main aspect of the invention it is characterised by a marker to be used inside a human or animal body, comprising an elongated wire of a radiation retarding material, wherein the wire is arranged with at least one bending means, capable of bending the wire upon insertion in body tissue.

By using a thin wire, a thin guide needle for insertion of the wire can be used, which reduces the risk of internal bleeding and infections as well as reduces or omits the need for anaesthesia. Because the wire is arranged with bending means, it will bend and stop in the tissue into which it is inserted and subsequent feed of the wire will cause it to bundle, thereby creating a marker with a mass that is visible when radiated. The bundling also causes the marker to attach to the tissue, thereby preventing migration of the marker.

The marker wire is thin, in the region of 0.1 to 0.4-0.5 mm and preferably around 0.3 mm and preferably arranged with material reduction at certain locations along the length of the wire, acting as bending points. The reduction of material can be placed such that the produced marker obtains a unique appearance, distinguishable from other markers in the vicinity. Several markers may be placed in the same penetration channel either separated from each other or together to form an even larger marker, i.e. tailored in situ with an appearance suitable for the actual case and application.

Because it attaches to the tissue and is of inert material, it can be left in the body after treatment. This is also an advantage for subsequent follow-ups of the treatment of tumours.

By using a tool adapted to the marker according to the invention the insertion and creation of the markers are simplified. By using appropriate marking on the tool, the user has information regarding the length of the marker, the penetration needle and the mandrin pushing the marker out of the needle.

These and other aspects of and advantages with the present invention will become apparent from the following detailed description of the invention and from the accompanying drawings.

BRIEF DESCRIPTION OF THE DRAWINGS

In the following detailed description of the invention, reference will be made to the accompanying drawings, of which FIG. 1a-d are different possible embodiments of a marker wire according to the present invention.

DETAILED DESCRIPTION OF THE INVENTION

The present invention relates to a marker for locating tumours or positions where tumours have been located. The marker is intended to be inserted in human or animal tissue and when the patient is radiated, the marker is visible on the produced image.

The marker according to the present invention comprises a thin wire 10, FIG. 1, of metal and/or alloys that is not harmful to human tissue. The metal could for example be silver, platinum or preferably gold. Gold is a good choice when high energy (megavolt) radiation beams are used for imaging. When such high energy is used it is only the mass that determines the retardation effect.

The wire is arranged with at least one, preferably a number of so called bending means 12, the purpose of which will be described below.

The wire is inserted into a tumour or a location where a tumour has been placed with the aid of a thin hollow sterile needle 14, FIG. 2. For guidance in positioning the tip of the needle, ultra-sound or computer tomography can be used. The needle that is used with the present invention is much thinner than the conventionally used needles for markers. The markers used today have a diameter of about 1.0-1.2 mm which requires a thick needle.

The wire according to the present invention has a diameter in the region of 0.1 mm to 0.4 mm, preferably about 0.3 mm, which means that the needle has an outer diameter of about 0.5 mm. Such a thin needle may be inserted into human tissue without the need for narcosis or local anaesthesia.

The needle can during insertion arranged with the wire inside the needle, but the needle can also be inserted with a mandrin inside the needle to reduce bending of the needle during insertion. After positioning of the needle tip the mandrin is withdrawn to check if the needle tip is in a blood vessel, then a marker wire is inserted. When the marker is to be placed in the human tissue, a guide wire, a mandrin 16, is arranged inside the needle, with which the wire is pushed out of the needle.

As mentioned above the wire is arranged with a number of bending means. FIGS. 1a-1d show different examples of these means. According to the examples of FIGS. 1a and 1b, at certain locations along the wire material has been removed, causing weakening of the wire at these locations.

Figure 2A:
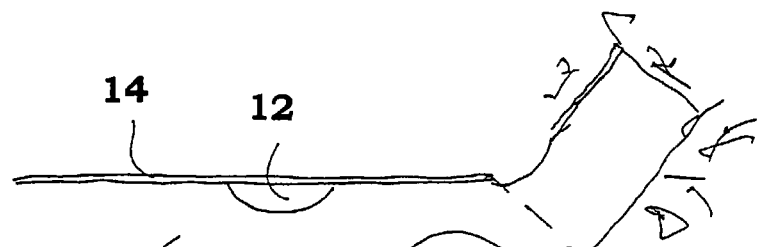
FIG. 2a-c is a schematic example of how a marker can be created.
Figure 2B:
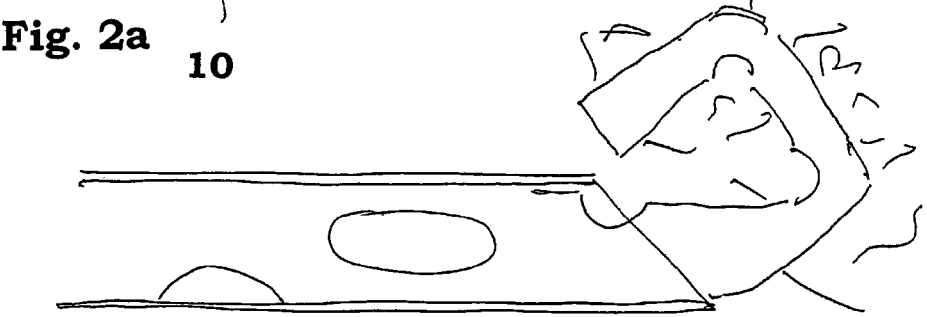
Figure 2C:
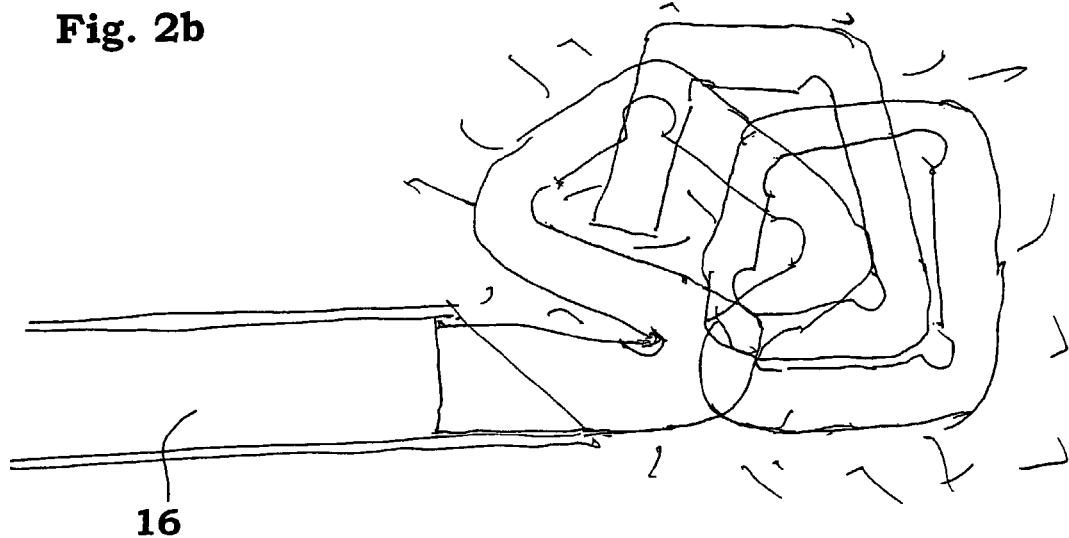
Figure 3A:
FIG. 3a-e are different examples of markers created by the marker wire according to the invention.
Figure 3B:
Figure 3C:
Figure 3D:
Figure 3E:

When the thin wire meets tissue its movement is stopped and the wire is bent due to the removed material FIGS. 2a-c, i.e. they act as bending points for the wire. As the wire is pushed further into the tissue it is bent several times because of the deflecting means and forms a bundle or cluster of bent wire, becoming a dense marker with a certain mass, FIG. 2c. It is of course possible to arrange a larger weakening at the beginning of the wire, creating a "start" bend, and thus a stop of the movement of the wire in the tissue. Further advancement of the wire into the tissue will cause it to bend because of the resistance.

It is to be understood that the bending means, causing the wire to bend and bundle, could be achieved in many ways. For example the front end of the wire could have a different direction than the longitudinal direction of the wire, causing the wire to bend when the front end comes in contact with tissue, FIG. 1c, or a longitudinal slit, FIG. 1d whereby the "arms" on each side of the slit deflect and bend in different directions causing a resistance of the wire against further advancement of the wire. Instead, subsequent lengths of the wire that are pushed into the tissue will bend and form a bundle and thus a marker.

It is of course also possible to introduce and create more than one marker in the same penetration channel of the needle, see for example FIGS. 3a-e. The length of each wire may also be altered depending on the actual application and modified in situ with an appearance that is suitable for the actual application. One part of the marker wire may for example be left unbent in order to create a "tail" image together with the bundled marker. The markers can thus be formed with individual appearances at specific locations such that they may be distinguishable from other markers that are placed in the vicinity in a three-dimensional way.

Figure 4:
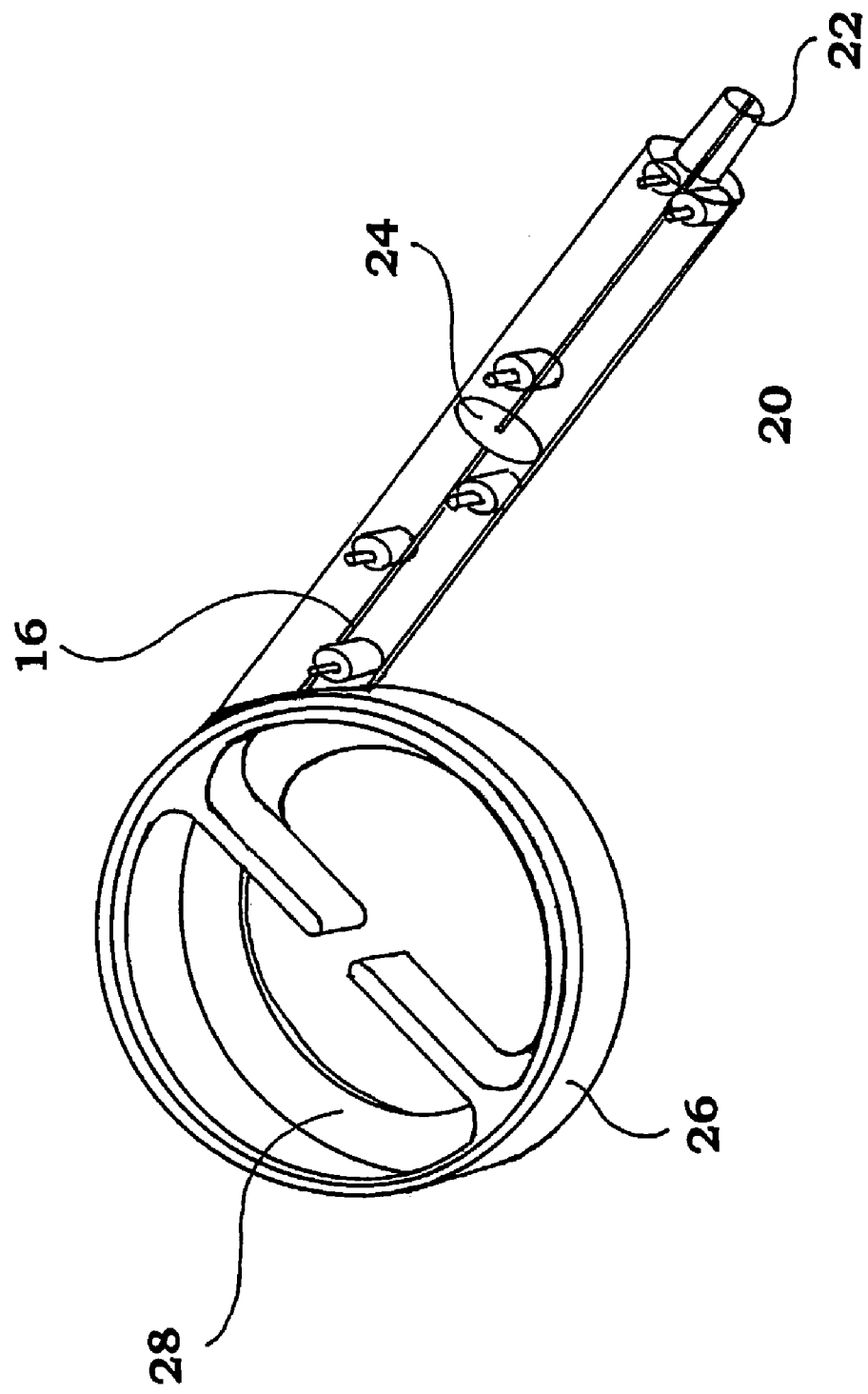
FIG. 4 is a tool arranged to facilitate the insertion and creation of a marker according to the invention.

In order to facilitate the insertion, handling and creation of a marker according to the present invention, a handling device or tool has been designed, see FIG. 4. It comprises an elongated tube-like part 20 having a front end with a narrow part 22. Inside the tube a number of guides 24 are arranged. The guides hold a tube/cannula containing the marker wire. A housing part 26 is connected to the tube, having a general ring-shape. Inside the ring a rotator 28 is rotatably arranged. A mandrin 16 is wound in a groove running around the outer periphery of the rotator. The mandrin extends into the tube/cannula a distance behind the marker wire when the rotator is mounted in the housing.

By turning the rotator after connection of the handling device to the fine needle it is easy to insert the marker wire and to form a bundle. Preferably the rotators are marked so that the user knows the length of the needle and where the length of the mandrin is adopted to reach the tip of the needle when the marker wire has been pushed into the tissue. The mandrin is attached to a hole in the rotator so that the rotator is stopped when the mandrin has been rolled out. Then the end of the mandrin is at the tip of the needle and cannot be moved further. Because of this the length of the needle has to correspond to the length of the mandrin. Therefore, preferably the device is pre-assembled and handled as a unit.

As mentioned above, the marker wire may be of a suitable metal, but it may also be of a non-inert material if the marker wire is intended to guide the surgeon where the tissue is to be removed, for example during operation of a breast tumour. The marker wire may also be of a radio-active material for guidance during surgery.

There is also a development of active markers that transmit impulses that can be used for detecting position with other means than x-ray. A conceivable solution is that such a marker is connected to the marker of the present invention so that it is locked in the tissue in the manner described above. A sort of combination marker is obtained, with bending capabilities, which is dense and has an active signal, for example an electro-magnetic signal.

An advantage with the marker according to the present invention is that the bundling ties the wire to the tissue, thereby preventing any movement or migration within the body of the patient. It is also possible to monitor possible re-growth of tumours at subsequent investigations if more than one is positioned in the previous tumour.

It is to be understood that the present invention is not limited to the embodiments described above and shown in the drawings but may be modified within the scope of protection of the patent claims.

The invention claimed is:

1. A marker which is inserted and then remains inside of a human or animal body, comprising:
    an elongated wire of a radiation retarding and/or radioactive material, wherein the wire includes several reductions of material along said wire configured to bend the wire into a bundle or cluster of bent wire upon insertion of the wire in body tissue, attach the bent wire bundle or cluster to the body tissue to prevent movement or migration thereof, and form the bent wire bundle or cluster into a dense marker with a certain mass that visibly appears as a single dense marker when radiated.

2. A marker according to claim 1, wherein said wire has a cross-sectional diameter in the range 0.1 to 0.5 mm.

3. A marker according to claim 2, wherein said wire has a diameter of 0.3 mm.

4. A marker according to claim 1, wherein said wire is made of gold.

5. A marker according to claim 1, wherein the wire further includes a start bend member at a front end thereof which, upon meeting the body tissue, is configured to resist further movement of the front end such that a remaining portion of the wire forms the bent wire bundle or cluster upon insertion in the body tissue.

6. A marker according to claim 5, wherein the start bend member is a length of the front end of the wire which is bent in a direction different from a longitudinal direction of the wire.

7. A marker according to claim 5, wherein the start bend member is a longitudinal slit at the front end of the wire which defines arms on each side of the slit which are configured to bend in different directions upon meeting the body tissue.

8. A marker according to claim 1, wherein each of said several reductions of material along said wire is present at a different peripheral location relative to a peripheral location of an adjacent said reduction.

* * * * *